United States Patent [19]

Brajnovic et al.

[11] Patent Number: 4,906,420
[45] Date of Patent: Mar. 6, 1990

[54] METHOD FOR PRODUCING PROSTHETIC CONSTRUCTIONS

[75] Inventors: Izidor Brajnovic, Göthenberg; Ingrid Tilly; Hans Würth, both of Tidaholm, all of Sweden

[73] Assignees: Nobelpharma AB; AB Novel Plast, Sweden

[21] Appl. No.: 197,073

[22] Filed: May 18, 1988

[30] Foreign Application Priority Data

May 22, 1987 [SE] Sweden .............................. 8702128-3

[51] Int. Cl.[4] .................. A61C 13/20; B32B 31/14
[52] U.S. Cl. .................................... 264/17; 264/134; 264/137; 264/156
[58] Field of Search .................... 264/17, 18, 103, 134, 264/137, 16, 154, 156

[56] References Cited

U.S. PATENT DOCUMENTS

| | | | |
|---|---|---|---|
| 1,899,521 | 2/1933 | Nudell | 264/17 X |
| 1,964,202 | 6/1934 | Hooper | 264/103 |
| 2,314,674 | 3/1943 | Walton | 264/17 |
| 2,341,604 | 2/1944 | Dresch | 264/17 X |
| 2,579,960 | 12/1951 | Pita et al. | 264/17 X |
| 2,750,318 | 6/1956 | LaGranda et al. | 264/18 |
| 2,848,750 | 8/1958 | Sannecke et al. | 264/17 |
| 3,022,210 | 2/1962 | Philipps | 264/103 X |
| 3,979,493 | 9/1976 | Cameron et al. | 264/137 X |
| 4,160,055 | 7/1979 | Reed | 264/137 X |
| 4,298,562 | 11/1981 | Latty | 264/103 |
| 4,584,152 | 4/1986 | Leach | 264/103 |
| 4,676,942 | 6/1987 | Ollivier et al. | 264/257 |
| 4,714,467 | 12/1987 | Lechmer et al. | 264/137 X |
| 4,770,832 | 9/1988 | Okamoto et al. | 264/103 |
| 4,776,865 | 10/1988 | Allaire | 264/103 X |

OTHER PUBLICATIONS

N. Björk et al, "Implant-fixed, dental bridges from Carbon/graphite fibre reinforced poly(methmethacrylate)" in Biomaterials 1986, vol. 7, Jan., pp. 73–75.

Primary Examiner—Jan H. Silbaugh
Assistant Examiner—Karen D. Kutach
Attorney, Agent, or Firm—Pollock, Vande Sande & Priddy

[57] ABSTRACT

Oral and extraoral prosthetic constructions of composite material with considerable fiber content, and in particular, jawbone anchored dental bridges of reinforced plastic, are made by the following method. A number of mutually retracted tubularly braided fibers (1), possibly in combination with continuous fiber strands, so-called roving, together constitute a fiber system which is packed in a tube, hose (2) or the like which is sealed and serves as outer packaging. A suitable matrix material, for example acrylic plastic, is injected into the hose for impregnation (wetting) of the enclosed fiber system, whereafter the hose (2) is removed. The fiber system is then polymerized to form a finished prosthesis blank in a mold. The prosthesis blank is then given suitable form and appearance by conventional after treatment.

8 Claims, 6 Drawing Sheets

METHOD FOR PRODUCING PROSTHETIC CONSTRUCTIONS

TECHNICAL FIELD

The present invention relates to a method for producing oral and extra-oral prosthetic constructions of composite material with a considerable fiber content, and in particular to the production of jawbone-anchored dental bridges in a fiber-reinforced plastic material.

BACKGROUND ART

Osseointegrated dental implant bridges have been clinically used with good results for more than 20 years, see for example Brånemark/Zarb/Albrektsson: "Tissue-Integrated Prostheses", Quintessence Books, 1985.

Such a bridge construction is anchored in the jawbone by means of a plurality of helical anchorage elements of titanium, so-called fixtures, on which fistular spacers are then disposed for anchoring the prosthesis proper. The bearing skeleton of a prosthetic construction, for example a dental bridge, is normally entitled the suprastructure and has hitherto been produced pursuant to prior-art casting technology in metal. The clearly dominant alloy which has been employed in such instance within Swedish dental care includes noble metals such as gold, platinum and palladium.

Because of the high material costs and the complex production procedure, such prosthetic constructions are extremely expensive.

In the article

N. Björk, K. Ekstrand and I. E. Ruyter: "Implant-fixed dental bridges from carbon/graphite fibre reinforced poly (methyl methacrylate) in Biomaterials 1986", Vol 7, January, pp. 73–75, the production has also been suggested of prosthetic bridge constructions in fiber-reinforced plastic. According to the method described therein, the bridge construction is built up such that the carbon fibres are wound around special titanium cones and then embedded in a polymer. However, such a method is highly circumstantial and does not give the sought-after controllable high fiber content.

OBJECT OF THE INVENTION

The object of the present invention is to realize a method for the production of prosthetic constructions of composite material which is simple and time-saving, which is environmentally safe and which entails minimal contamination of the fiber material. Furthermore, the method according to the present invention is to be well adapted to conventional odontological methodology and makes for good control of fiber content and structure. This latter is important for guaranteeing foreseeable mechanical (in terms of strength) and bio-compatible properties.

BRIEF DESCRIPTION OF THE ACCOMPANYING DRAWINGS

The nature of the present invention and its aspects will be more readily understood from the following brief description of the accompanying drawings, and discussion relating thereto.

In the accompanying drawings:

FIGS. 1–12 illustrate different phases in the method of approach for producing a fiber-reinforced implant-fixed dental bridge.

DESCRIPTION OF PREFERRED EMBODIMENT

Figure 1:
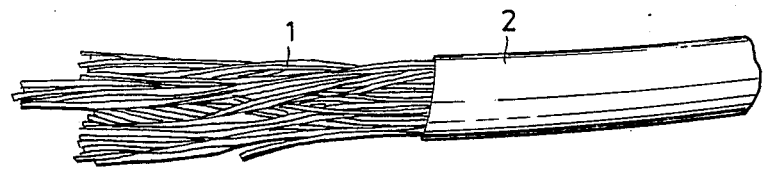

Referring to the drawings, FIG. 1 shows the starting material for producing an oral prosthetic construction in the form of a jawbone implant-fixed dental bridge. A suitable number of mutually retracted tubularly entwined fibers 1, possibly combined with continuous fiber strands, so-called roving, together constitute a fiber system. Both organic and inorganic fibers such as aramide fibers, carbon fibers, glass fibers or ceramic fibers are conceivable as reinforcing materials. The fibers are pretreated and handled in accordance with suppliers' instructions or in accordance with prior art processes. The fiber system is further drawn into a plastic hose or plastic tube 2 which may be sealed at both ends and serve as transport packaging.

Figure 2:
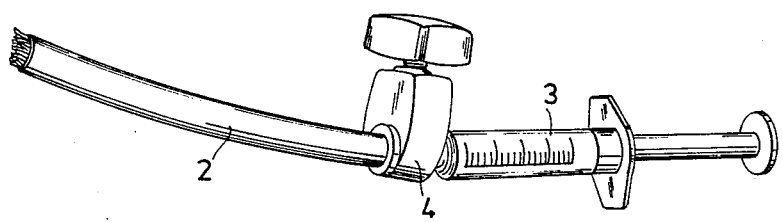
Figure 3:
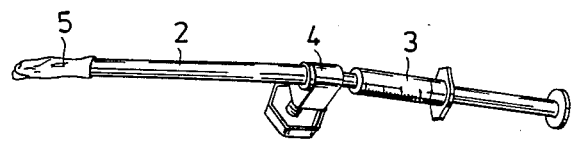

The plastic hose provides a practical and flexible package for the fiber system. Packaging of desired length can be supplied to dental technician laboratories where the prosthesis is to be produced. There, a length of the hose corresponding to the desired length of the dental bridge is cut off. An injection cylinder or other injection equipment 3 filled with a suitable matrix material is connected to the hose with the fiber system, see FIG. 2. Injection of the matrix material must be effected slowly, under pressure and/or vacuum at a uniform rate in order to attain complete impregnation of the fibers. As matrix material, for example a lightly prepolymerized acrylic plastic serves adequately. Such acrylic plastics, as well as injection technology, are well known in the art and will not, therefore, be described in greater detail here. In order to obtain a reliable, tight connection of the injection equipment 3 to the hose, the hose is provided with a suitable clamping device 4 which closes about the circumference of the hose. The other end of the hose is closed by tape or the like 5 which prevents the fiber system from migrating out of the plastic hose on injection of the plastic, see FIG. 3. However, the closure is arranged such that air may be allowed to depart from the fiber system when the fibres are impregnated (wetted) by the plastic.

Figure 4:
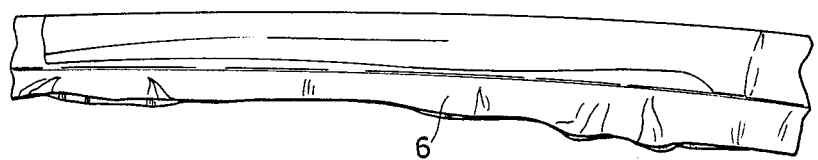

The plastic hose or plastic tube 2 has now fulfilled its function and the impregnated reinforcing package may be transferred from the plastic hose to, for example, a plastic film 6 in the form of a thin-walled hose which accommodates the reinforcing package, see FIG. 4. The hose is sealed at both ends such that the reinforcing package of a suitable length for a dental bridge is wholly enclosed.

Figure 5:
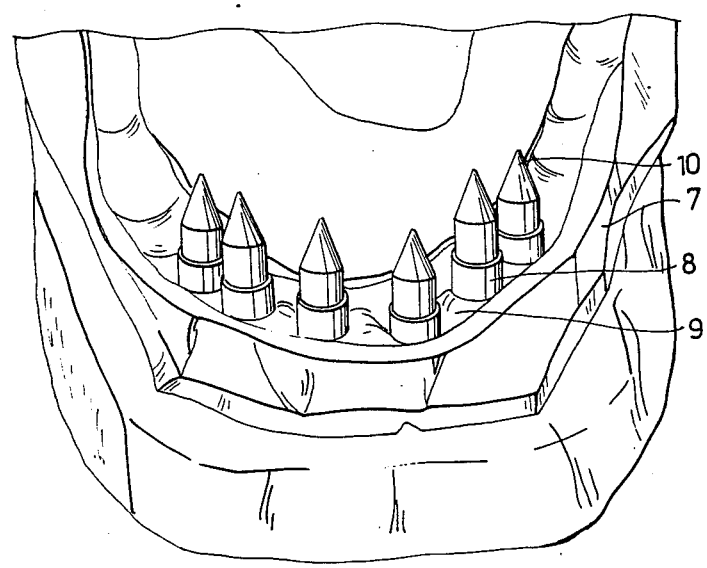

The impregnated reinforcing package—which is lightly flexible—is now passed into a mold 7 of per se known type, see FIG. 5. Retention-provided metal caps 8 (cylinders) are positioned in the mold, these corresponding to the disposition of the spacer members in the jawbone-anchored dental bridge. The reinforcing package is to be applied in a curved recess 9 in which the metal caps 8 protrude. To facilitate this operation, tips 10 have been passed on the guide pins of the metal caps such that the reinforcing package may more readily be perforated and open the way for the metal caps through the fiber system.

Figure 6:
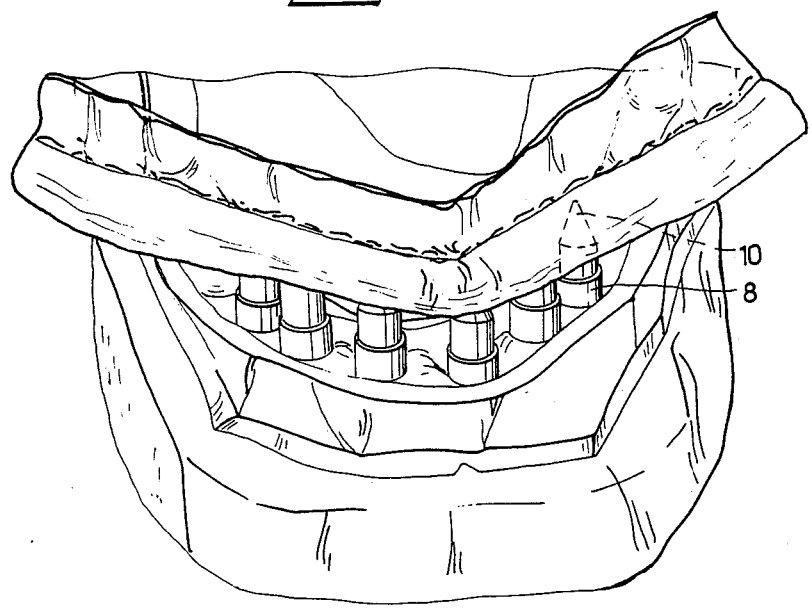

Once the fiber system has been provided with perforation indications, it is removed from the mould, see FIG. 6, and provided with holes for the metal caps 8.

Such holes are made manually using a suitable tool, an awl or the like.

Figure 7:
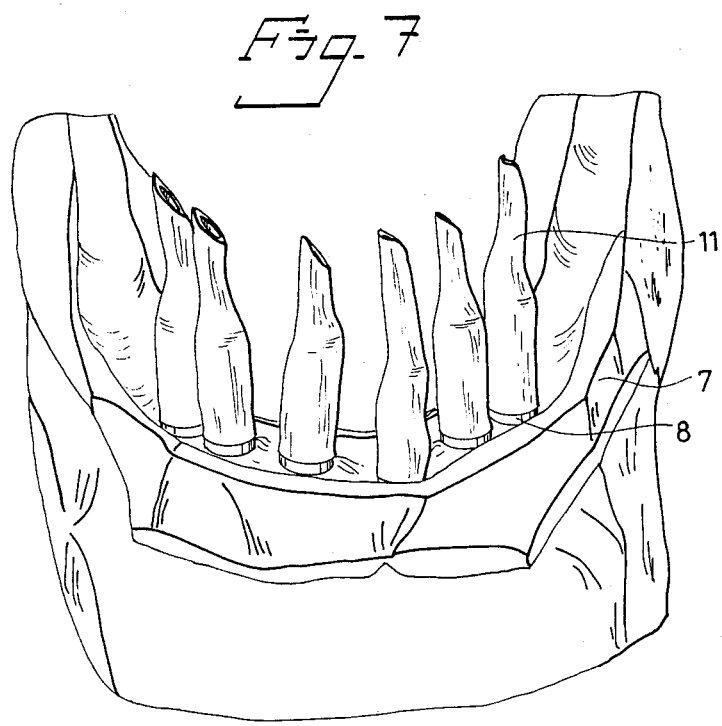

FIG. 7 shows the mold, the metal caps 8 having been provided with plastic sleeves 11 of shrink-on material which have been passed over the cylindrical metal caps. The sleeves prevent the fiber from becoming attached and packing to the upper retentions of the metal caps, and the sleeves thus permit the fibers to come into abutment with the bottom of the recess 9.

Figure 8:
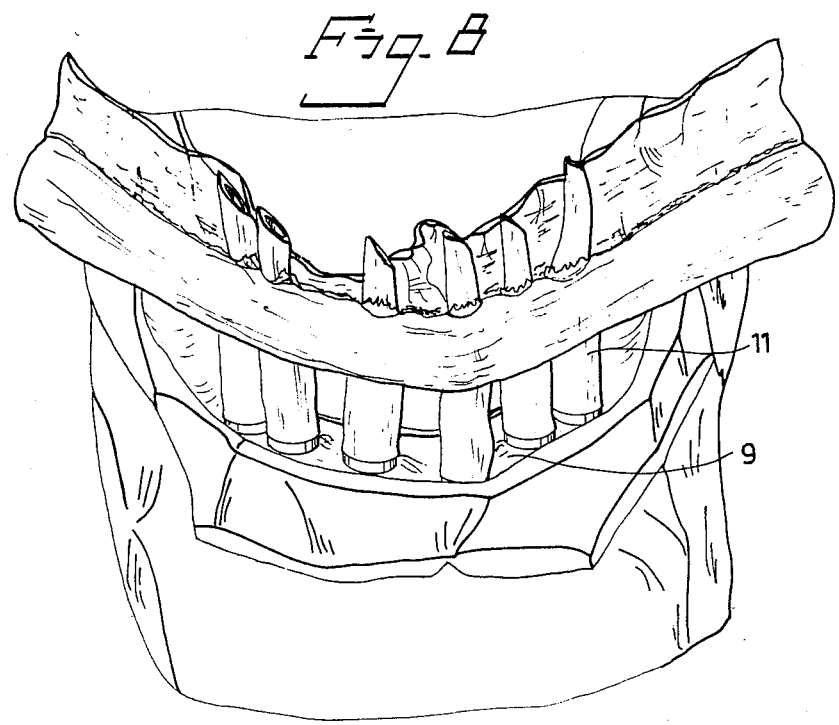

FIG. 8 shows how the flexed fiber system is passed onto the plastic sleeves 11 and applied against the bottom of the recess 9. The plastic sleeves 11 are thereafter removed so as to make possible contact between the impregnated fiber system and the retentions of the metal caps in the form of external threading or the like. Further plastic is added to those holes left by the plastic sleeves in the fiber system.

Figure 9:
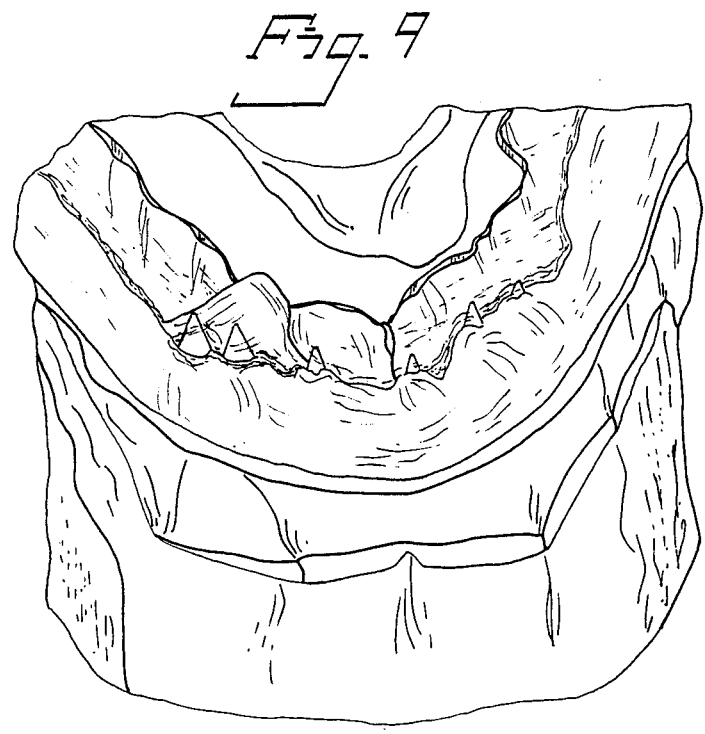
Figure 10:
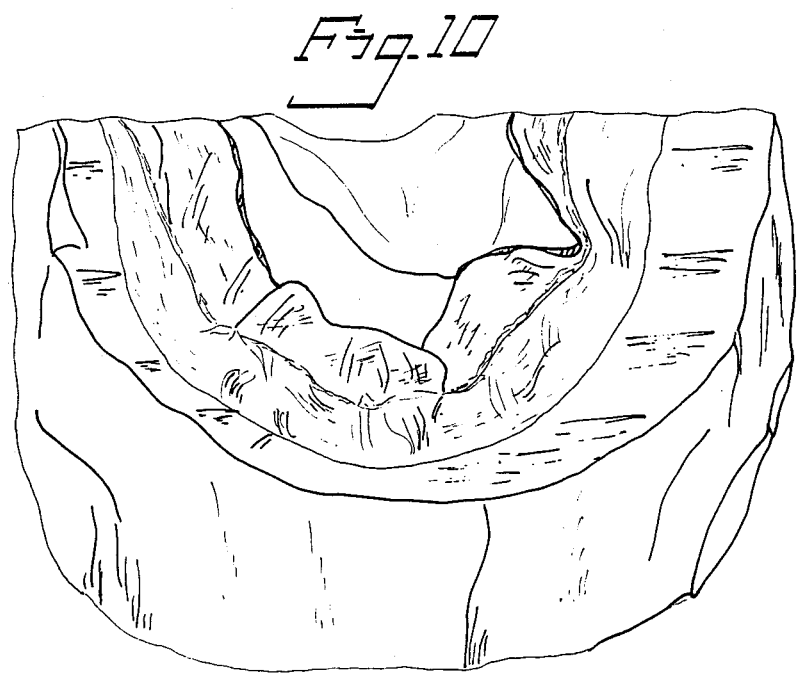

FIGS. 9 and 10 illustrate the application of the lingual and buccal precast, respectively, which are glued in place. Such precasts are also previously known in dental technology and will not, therefore, be described in greater detail here.

Thereafter, for example a silicon top is disposed on the opening over the impregnated fiber system which is allowed to polymerize. After polymerization, the top is removed, approx. 2 mm of the top is cut away on that surface which abutted against the subjacent precasts, such that an implant over the fiber system will achieve primary contact therewith. The implant is pressed against the precasts by means of tightened hose clamps, rubber bands or the like to achieve a continuous pressure on the fiber system. As a result, the shrinkage of the plastic will be compensated for such that no air or water is entrapped in the finished prosthesis construction.

The polymerization is effected in accordance with prior art methods. Thus, the entire mold combination is placed in a heating apparatus, water bath or pressure vessel or oven for hot polymerization of the plastic. After the polymerization, the entire package is allowed to cool slowly, the precasts are removed and the raw blank for a fiber-reinforced dental bridge has been obtained.

Figure 11:
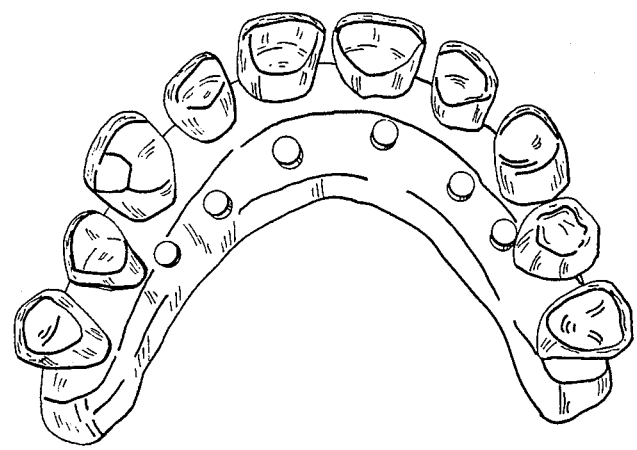

The dental bridge is given suitable form and color, it is lacquered with, for example, a pink coating lacquer if required, and teeth are applied using the precast for the disposition of teeth. The teeth are fixed on the dental bridge using pink or tooth-colored auto- or pressure-polymerizing acrylic plastic of high quality. It is important that the polymerization take place at a temperature which exceeds the glazing temperature of the acrylic plastic in a pressure vessel with the bridge fixedly screwed to the plaster model. After polymerization, the precast is removed, the bridge is unscrewed and cleaned according to a prior art method, see FIG. 11.

Figure 12:
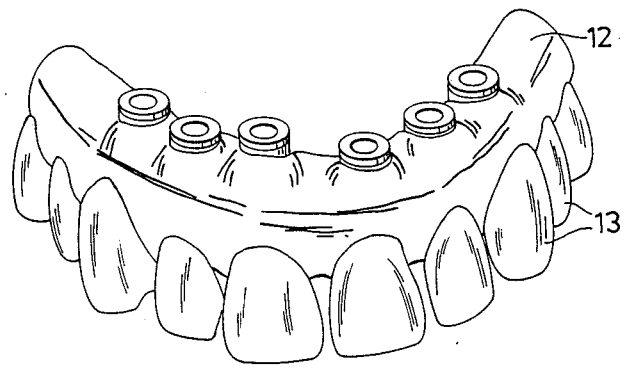

Finally, FIG. 12 shows the finished jawbone-anchored dental bridge 12 with teeth 13 and arranged to be anchored in place by means of spacers on the fixtures which have healed into the jawbone. It might be mentioned that, instead of simply lacquering the prosthesis in conjunction with after-treatment, a pinkcolored surface sock of fiber material may be applied around the fiber system from the beginning. Yet a further alternative is to employ a colored plastic matrix.

The above-described method for producing jawbone-anchored dental bridges of composite material results in constructions of high and readily controllable fiber content, which, together with an excellent fiber impregnation, afford extremely good mechanical properties. In addition, the method results in an environmentally safe product with low contents of residual monomer.

There will be presented below an account of the tests and analyses which have been conducted on sample rods manufactured according to the method described above. The thus manufactured sample rods have been compared with the blank for a dental bridge produced according to conventional methods.

Manufacture of specimen rods was effected according to the following steps:

Reinforcing package was manufactured and a suitable length thereof was drawn into a hose.

Acrylic resin plus setting agent mixed in a beaker and deaerated.

Injection of resin by means of injector into the hose.

The resin-impregnated reinforcements is passed down into the mold.

The mold is filled with further resin, if applicable.

Mold release agent/shrink-on film and top applied under pressure.

Prepolymerization effected at 50°-60 C. overnight, the rods being removed from the mold and after-cured at 120° C. for a few hours.

Those specimen rods which were manufactured and also analyzed have the following composition:

A. Matrix: Prepolymerized polymethyl methacrylate (PMMA) as above.

Reinforcement: Two carbon fibers braided in one another with 36 carbon fiber roving inside.

B. Matrix as per A.

Reinforcement: Two Nextel braids in one another with 24 carbon fiber roving inside.

These were compared with a sample specimen (C) of carbon fiber braid reinforced PMMA in which the matrix was produced of MMA and a powder containing PMMA and initiator.

RESULT OF TEST AND ANALYSIS

Ash test

The fiber contents were determined by ash test over open flame. A conversion to volume per cent gave the following results:

| Sample | $V_f\%$ |
|--------|---------|
| A      | 63      |
| B      | 56      |
| C      | 9.1     |

3-point bending

The moduli of elasticity were determined from the results of 3-point bending in accordance with ASTM D 790. The specimen rods A and B were of semi-circular cross section, while specimen rod C was of rectangular cross section.

| Sample | E GPa |
|--------|-------|
| A      | 122   |
| B      | 47    |
| C      | 7.5   |

However, it should here be observed that in the case of C it was not possible to follow the norm as regards distance between supports. The distance according to the norm was, here, 3.5 times greater than that employed.

DSC

DSC analysis was carried out in the range of between 50 and 200° C. Both a first and second run were registered. This analysis gives the glazing temperature of the material and the presence of any possible residual monomer.

A: Tg=104° C. (2nd run). No residual exotherm registered.

C: Tg=103° C. (2nd run). Residual exotherm manifest.

What we claim and desire to secure by letters patent is:

1. A method for the production of oral and extraoral prosthetic constructions of composite material having considerable fiber content, which comprises:
   bunching or braiding together a plurality of fibers to form an elongate fiber system;
   packing said elongate fiber system in a tube wherein said tube is closed and sealed to serve as transport packaging for said elongate fiber system;
   supplying lengths of said packed tube to where said prosthetic constructions are produced, and preparing desired lengths of said packed tube for injection of a matrix material;
   injecting into said packed tube said matrix material for completely impregnating said elongate fiber system;
   removing said tube from said impregnated elongate fiber system, and applying said elongate fiber system impregnated with said matrix material to a mold;
   causing said matrix material to polymerize to thereby form a prosthesis blank;
   subjecting said prosthesis blank to aftertreatment to provide an oral or extraoral prosthetic construction.

2. The method claim 1 wherein said matrix material is an acrylic plastic.

3. The method of claim 1 wherein prior to causing said matrix material to polymerize, said elongate fiber system is enclosed in a thin-walled hose of plastic.

4. The method of claim 1 wherein said mold includes metal caps and wherein said elongate fiber system prior to applying it to said mold is provided with holes that correspond to the positions of said metal caps.

5. The method of claim 4 which further comprises providing said metal caps, prior to applying said elongate fiber system to said mold, with plastic sleeves for facilitating penetration of said metal caps in said holes of said elongate fiber system.

6. The method of claim 4 wherein said metal caps are upstanding in said mold and are provided with removable tips for providing perforation indications on said elongate fiber system upon passing down of said elongate fiber system into said mold.

7. The method of claim 6 which further comprises removing said tips prior to causing said matrix material to polymerize, whereby said elongate fiber system will come into direct contact with said metal caps.

8. The method of claim 7 wherein said metal caps are provided with retention means in the form of an external thread for improving contact between the surface of the metal caps and the individual fibers in said elongate fiber system.

* * * * *

UNITED STATES PATENT AND TRADEMARK OFFICE
CERTIFICATE OF CORRECTION

PATENT NO.  : 4,906,420
DATED       : March 6, 1990
INVENTOR(S) : Izidor Brajnovic, et al.

It is certified that error appears in the above-identified patent and that said Letters Patent is hereby corrected as shown below:

On the cover page, change the line "[75] Inventors: Izidor Brajnovic, Göthenberg;...." to --- [75] Inventors: Izidor Brajnovic, Göteborg;.... ---.

Same page, change "[73] Assignees: Nobelpharma AB; AB Novel Plast, Sweden" to --- [73] Assignees: Nobelpharma AB; AB Nobel Plast ---.

Signed and Sealed this

Tenth Day of December, 1991

Attest:

HARRY F. MANBECK, JR.

*Attesting Officer*   *Commissioner of Patents and Trademarks*